United States Patent [19]
Blumenthal et al.

[11] Patent Number: 4,814,061
[45] Date of Patent: Mar. 21, 1989

[54] HOT GAS MEASURING PROBE

[76] Inventors: Robert N. Blumenthal, 17470 Bard Ct., Brookfield, Wis. 53005; Andreas T. Melville, 204 N. 86th St., Milwaukee, Wis. 53226

[21] Appl. No.: 128,061
[22] Filed: Dec. 3, 1987
[51] Int. Cl.[4] ............................................. G01N 27/58
[52] U.S. Cl. ..................................... 204/410; 204/428
[58] Field of Search ................ 204/427, 428, 429, 1 S, 204/410

[56] References Cited

U.S. PATENT DOCUMENTS

| | | | |
|---|---|---|---|
| 4,101,404 | 7/1978 | Blumenthal et al. | 204/428 |
| 4,186,072 | 1/1980 | Blumenthal et al. | 204/428 |
| 4,193,857 | 3/1980 | Bannister et al. | 204/428 |
| 4,290,586 | 9/1981 | Kane et al. | 266/80 |
| 4,396,792 | 8/1983 | Falk | 136/234 |
| 4,521,639 | 6/1985 | Falk | 136/234 |
| 4,588,493 | 5/1986 | Blumenthal et al. | 204/410 |
| 4,659,679 | 4/1987 | Falk | 501/99 |

OTHER PUBLICATIONS

David W. Richerson, pages 139, 141, 142, "Modern Ceramic Engineering", published by Marcel Dekker, Inc. 1982.
3M Nextel "Ceramic Fiber Products" for high temperature applications (brochure).

Primary Examiner—G. L. Kaplan
Attorney, Agent, or Firm—Fuller, Puerner & Hohenfeldt, S.C.

[57] ABSTRACT

An oxygen sensor is provided with an electrolyte tube formed in two parts, one part is an elongated tube and the other part is a sacrificial pellet which thermally insulates the tube from thermal shock which can cause cracks in the tube.

16 Claims, 1 Drawing Sheet

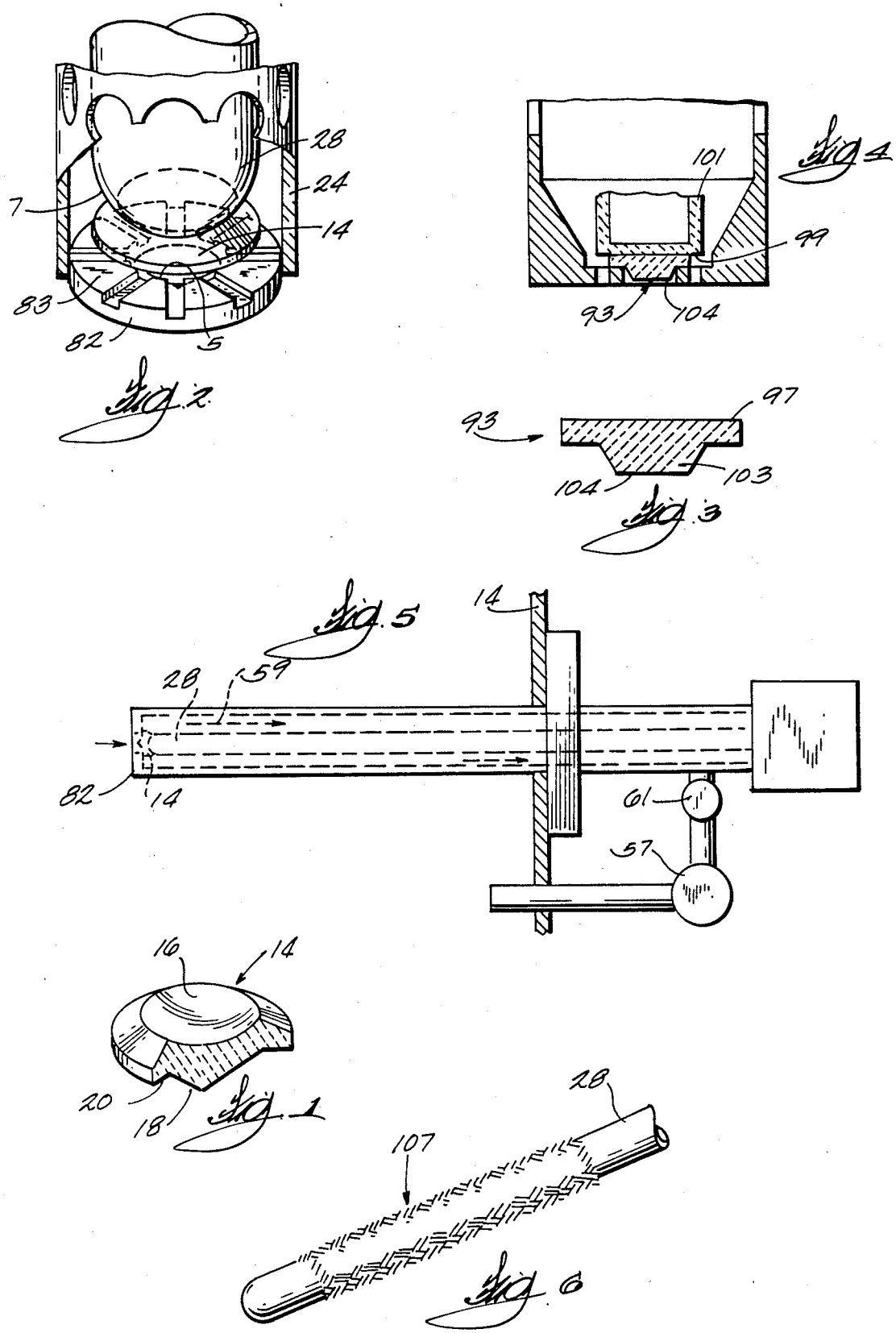

HOT GAS MEASURING PROBE

BACKGROUND OF THE INVENTION

Although the invention in U.S. Pat. No. 4,588,493 is effective to accomplish the intended result, some cracks in the electrolyte tube have occurred due to thermal shock resulting from non-uniform temperature gradients. For example, when the furnace temperature is lowered, the metal disk 82 in FIG. 1 of that patent quickly cools the tip or ball nose 7 of the electrolyte tube 28 in FIG. 2. The fast cooling occurs because the disk 82 which is metal, has a high thermal conductivity and consequently heat is rapidly removed from the tip of the ceramic electrolyte tube 28 which is in line contact with disk 82. In addition, when the furnace temperature is increased, the metal disk 82 initially heats up more rapidly than the ceramic electrolyte tube. In this case, heat flows from the metal disk to the surface of the ceramic electrolyte tube which is in line contact with the metal disk 82. Both of the above cases of cooling and heating of the furnaces produces a non-uniform temperature distribution at the tip of the electrolyte tube. This non-uniform temperature distribution produces a non-uniform thermal stress distribution at the tip of the electrolyte tube, (i.e., when the furnace temperature changes a temperature difference develops between the outside surface and the interior of the electrolyte tube). According to Richerson, *Modern Ceramic Engineering* published by Marcel Dekker, Inc., 1982, page 139, "Thermal shock refers to the thermal stresses that occur in a component as a result of exposure to a temperature difference between the surface and interior, or between various regions of the component." These thermal stresses can produce micro cracks in the tip of the electrolyte tube. It should also be noted, (e.g. see U.S. Pat. No. 4,101,404, Column 1, Lines 25–27), that the electrolyte tube which is a ceramic material, is hard and brittle, and is thus very susceptible to thermal shock. For example, if the oxygen probe is installed in a hot furnace, it must be slowly pushed into the furnace approximately at the rate of 1 inch/min. to avoid thermal shock. Also, if the oxygen probe is removed from a hot furnace, it is also important to remove it slowly (Approx. 1 inch/min.) to avoid thermal shock. Non-uniform temperature distributions that may produce cracks in the electrolyte tube from thermal shock can also be caused by thermal cycling. Thermal cycling results from the fluctuation in temperature of the radiant tube or other heat sources which supplies the heat to the furnace. The thermal cycling in conjunction with openings in the metal alloy sheath 17 in FIG. 1 of U.S. Pat. No. 4,588,493, will also produce a non-uniform temperature distribution on the electrolyte tube 28. Loading and/or unloading of work into the furnace will also cause non-uniform temperature distribution. If the electrolyte tube, which separates the reference air in the interior of the electrolyte tube from the furnace atmosphere, develops a crack, gas may leak through the crack and alter the gas composition locally at the electrode region. Any change in the gas composition that produces a change in the oxygen partial pressure will affect the voltage developed by the oxygen sensor and cause an error in its accuracy.

SUMMARY OF THE INVENTION

The invention provides a two part electrolyte with both parts constructed of essentially the same material. One part consists of the elongated tube and the other part is pellet shaped. However, the composition of the pellet and the manufacturing technique used to produce the pellet were selected to provide improved thermal shock characteristics to avoid the problems of the prior art electrolyte tube. Yet the pellet provides the line contact to obtain the benefits of the invention in U.S. Pat. No. 4,588,493. The pellet has better thermal shock characteristics but similar electrical properties to the electrolyte tube. Experimental tests have shown that satisfactory electrical contact for the accurate performance of the oxygen sensor is made when mechanical contact is made between the two part electrolyte pellet-electrolyte tube system. The electrolyte pellet is formed by pressing and pre-sintering the yittria doped Zirconia powder. The pellet is then machined and sintered at 1450° C. During the final sintering process, the pellet shrinks to its final size. In contrast, the gastight electrolyte tube is produced using a slip cast technique. One of the advantages of the two part electrolyte system is that the method of fabrication, and the electrolyte composition can each be selected to give the pellet superior thermal shock resistance compared to the electrolyte tube. Another advantage of the two part electrolyte system is that the pellet can act as a sacrificial component. For example, when the furnace temperature changes, the rapid heat exchanged between the electrode and the electrolyte is confined primarily to the pellet. Thus, the non-uniform temperature gradients and the associated thermal stresses would occur primarily in the pellet. The superior thermal shock resistance of the pellet would minimize the effect of these thermal stresses. However, even if cracks were eventually produced in the pellet, the performance of the oxygen probe would not be affected because the electrolyte tube would still be gas tight. Another feature of the invention is to use a thermal barrier to cover the electrolyte tube to minimize the rate of heat transfer during heating or cooling of the oxygen probe and thus avoid thermal shock of the electrolyte tube. The thermal barrier would be a material that would have a low thermal and electrical conductivity and good thermal shock resistance. Examples of suitable thermal barriers are a ceramic fiber sleeve, a thin ceramic tube or a ceramic material sprayed on the electrolyte tube.

Further objects, features and advantages of the invention will become apparent from the disclosure.

DESCRIPTION OF DRAWINGS

FIG. 1 is a fragmentary perspective view of the electrolyte pellet;

FIG. 2 is a fragmentary perspective view of the pellet in place in an oxygen probe;

FIG. 3 shows a modified embodiment of the pellet;

FIG. 4 shows the modified embodiment in a probe;

FIG. 5 is a further modified embodiment of the invention; and

FIG. 6 shows an electrolyte tube with an insulative jacket.

DESCRIPTION OF PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended thereto.

The present application relates to hot gas measuring probes of the type illustrated in U.S. Pat. No. 4,588,493 which is incorporated herein by reference. Also incorporated herein by reference are U.S. Pat. Nos. 4,101,404 and 4,186,072. As illustrated in U.S. Pat. No. 4,588,493, the hot gas probe includes an electrolyte tube 28 which in the present invention forms the first part of a two part electrolyte and a pellet 14 (FIG. 1, FIG. 2) which forms the second part of the electrolyte as hereinafter described.

Referring again to FIG. 2, the part 82 is an end plate or anode and comprises the second electrode. It is electrically connected to the circuit through either a metallic sheath 24 as shown in FIGS. 2, 4 and 5 or electrical lead wire as shown in FIG. 4 of U.S. Pat. No. 4,588,493.

In accordance with the invention, the electrolyte is formed in two parts to minimize the destruction of the electrolyte tube by thermal shock from non-uniform temperature gradients. The commercially available electrolyte tube 28 is fabricated using a slip cast technique. Whereas the electrolyte pellet 14 is produced by cold pressing the powdered electrolyte material into the form of a cylindrical rod, which is approximately ¾" in diameter by ¾" in length. The rod is then removed from the die and presintered at 1100° C. for 1 hour. During the presintering heat-up, the specimen is first pre-heated to 500° C. for 1 hour and then slowly heated (approximately 100° C. per hour) to 1100° C. where it is held for two hours. After presintering the rod to increase its mechanical strength, the rod is machined into the shape of the pellet shown in FIG. 1. The size of the machined pellet is larger than the final required size because of the shrinkage that occurs during the final sintering process. The machined pellets are then sintered at 1450° C. for 12 hours to produce the pellet shown in FIG. 1. The electrolyte powder is composed of $ZrO_2$ (Zirconia) doped with $Y_2O_3$ yittria in the range of 3 to 8 mole % $Y_2O_3$. The preferred composition is 3 mole % $Y_2O_3$, which is a partially stabilized zirconia. The bending strength of this composition with 3 mole % is approximately 1000 MPa, whereas with 8 mole % the bending strength is approximately 300 MPA in the specification data of one of suppliers of commercially available Zirconia powder. According to Richerson, *Modern Ceramic Engineering,* supra, page 142, partially stabilized zirconia is extremely thermal shock resistant. This composition is selected to improve the thermal shock resistance of the pellet relative to the electrolyte tube 28 which is fully stabilized and has a composition of 5.3 mole % $Y_2O_3$. The commercially available tubes from Coors Porcelain Co. of Golden, Colo. are 5.33 mole % $Y_2O_3$ and McDanel Refractory of Beaver Falls, Pa. is 6.2 mole % $Y_2O_3$.

The pellet 14 separates and thermally insulates the tube 28 from the line contact with the metal electrode 82 which changes temperature, more rapidly than the ceramic tube 28. The line contact of the electrolyte pellet 14 and the second electrode provides the advantages disclosed in U.S. Pat. No. 4,588,493. However, the rapid heat transfer along the line contact can provide a significant thermal gradient between the metal of electrode 82 and at the line contact and the corresponding material of the tube 28 which contacts the metal. The pellet 14 assists in maintaining the structural integrity of the tube 28 and minimizes micro cracks caused by thermally generated stresses.

Because the electrolyte is in two parts, any cracks in the pellet 14 will not cause gas leakage through the end of the tube 28.

As best shown in FIG. 1, the pellet has a recess 16 complementary in shape to the ball nose end 7 (FIG. 2) of the tube 28. This interfitting of the first and second parts provides broad based contact for effective electrical conduction. The pellet 14 (FIG. 2) is also provided with a conical surface or projection 18 which is sized to interfit in the aperture 5 of the second electrode 82. The portion 20 of the pellet that forms the side margin rests on the flat surface 83 of electrode 82 and prevents rocking of the pellet and helps center the pellet 14 in the appropriate position.

FIG. 3 shows a modified form of the pellet 93 provided with a flat surface 97 which mates with surface 99 of a flat electrolyte tube 101 (FIG. 4). The projecting part 103 has a flat end 104 rather than a pointed end as does the projecting surface 18 in FIG. 1. The probe in FIG. 4 corresponds to the probe in FIG. 3 of U.S. Pat. No. 4,588,493. The tube 28 is pressed against the pellet 14 which is in mechanical and electrical contact with the electrode end plate 82.

FIG. 5 shows a sampler in the wall of a furnace using the pump to draw gas into the system. The probe in FIG. 5 corresponds to probe in FIG. 8 of U.S. Pat. No. 4,588,493.

FIG. 6 shows a fiber protective sleeve 107 around an electrolyte tube 28. The sleeve 107 enables gas flow past the outer walls of the tube as in FIG. 5 but it slows down heat transfer and minimizes damage to tube 28 caused by thermal shock. It can be used alone or in combination with the pellet shown in FIGS. 2, 4 and 5.

I claim:

1. In an oxygen sensor for measuring the properties of a gas inside a furnace having a solid electrolyte means with an interior surface and an exterior surface for cooperation with first and second electrodes to generate a representative voltage; a first electrode in contact with the interior surface of the electrolyte; a second electrode having a surface in contact with the exterior surface of the electrolyte; conductor means for conducting a voltage generated between the first and second electrodes in correspondence with gas properties; and sheath means having a generally tubular wall surrounding the electrodes and electrolyte for supporting the electrodes and electrolyte within the furnace, and wherein said sensor includes:

a. means for supporting said second electrode on said sheath means;
   b. said second electrode and said electrolyte means having cooperating wall means defining gas passages to allow passage of gas past the points of contact of the second electrode and said electrolyte means and into the interior of the sheath means, said cooperating wall means providing a line contact of a metal electrode and electrolyte, and said gas passages affording adequate gas exchange at the line contact between the electrolyte and second electrode to minimize chemical reactions and provide representative measurements, the improvement wherein said electrolyte means is formed of two parts with said first part being in electrical contact with said first electrode and said second part being separable from said first part and said second part being in electrical contact with said second electrode and said second part thermally insulating said first electrolyte part from said line contact and said second part having superior thermal shock resistant properties as compared with said first part to minimize deterioration of said second part due to thermal stress.

2. The improvement of claim 1 wherein said electrolyte first part has a distal end and wherein said second part has a electrolyte contacting surface complementary in shape to said distal end.

3. The improvement of claim 2 wherein said distal end is ball nosed and said complementary surface of said second part has a recess which receives said ball nosed end.

4. The improvement of claim 1 wherein said second electrode has an aperture and said second part has a surface projecting into said aperture.

5. The improvement of claim 4 wherein said surface is conical in configuration.

6. The improvement of claim 1 wherein said first electrolyte part is an elongated tube and a heat resistant fiber jacket surrounding part of said tube.

7. In an oxygen sensor for measuring the properties of a gas inside a furnace having a solid electrolyte means with an interior surface and an exterior surface for cooperation with first and second electrodes to generate a representative voltage; a first electrode in contact with the interior surface of the electrolyte; a second electrode having a surface in contact with the exterior surface of the electrolyte; conductor means for conducting a voltage generated between the first and second electrodes in correspondence with gas properties; and sheath means having a generally tubular wall surrounding the electrodes and electrolyte for supporting the electrodes and electrolyte within the furnace, and wherein said sensor includes:
  a. means for supporting said second electrode on said sheath means;
  b. said second electrode and said electrolyte means having cooperating wall means defining gas passages to allow passage of gas past the points of contact of the second electrode and said electrolyte means and into the interior of the sheath means, and said gas passages affording adequate gas exchange at the contact between the electrolyte and second electrode to minimize chemical reactions and provide representative measurements,
  the improvement wherein said electrolyte means is formed of two parts with said first part being in electrical contact with said first electrode and said second part being separable from said first part and said second part being in electrical contact with said second electrode and said second part being located intermediate said first part and said second electrode and thermally insulating said first electrolyte part from said second electrode and said second part having a higher strength and superior thermal shock resistant properties as compared with said first part to minimize deterioration of said second part due to thermal stress and to protect the first part.

8. The improvement of claim 7 wherein said electrolyte first part has a distal end and wherein said second part has an electrolyte contacting surface complementary in shape to said distal end.

9. The improvement of claim 8 wherein said distal end is ball nosed and said complementary surface of said second part has a recess which receives said ball nosed end.

10. The improvement of claim 7 wherein said second electrode has an aperture and said second part has a surface projecting into said averture.

11. The improvement of claim 10 wherein said electrode second part surface is conical in configuration.

12. In an oxygen sensor for measuring the properties of a gas inside a furnace having a solid electrolyte means with an interior surface and an exterior surface for cooperation with first and second electrodes to generate a representative voltage; a first electrode in contact with the interior surface of the electrolyte; a second electrode having a surface in contact with the exterior surface of the electrolyte; conductor means for conducting a voltage generated between the first and second electrodes in correspondence with gas properties; and sheath means having a generally tubular wall surrounding the electrodes and electrolyte for supporting the electrodes and electrolyte within the furnace, and wherein said sensor includes:
  a. means for supporting said second electrode on said sheath means;
  b. said second electrode and said electrolyte means having cooperating wall means defining gas passages to allow passage of gas past the points of contact of the second electrode and said electrolyte means and into the interior of the sheath means, and said gas passages affording adequate gas exchange at the contact between the electrolyte and second electrode to minimize chemical reactions and provide representative measurements,
  the improvement wherein said electrolyte means is formed of two parts with said first part being in electrical contact with said first electrode and said second part being separable from said first part and said second part being in electrical contact with said second electrode and said second part being located intermediate said first part and said second electrode and thermally insulating said first electrolyte part from said second electrode said second part being replaceable after use independently of the first part.

13. In an oxygen sensor for measuring the properties of a gas inside a furnace having a solid electrolyte means with an interior surface and an exterior surface for cooperation with first and second electrodes to generate a representative voltage; a first electrode in contact with the interior surface of the electrolyte; a second electrode having a surface in contact with the exterior surface of the electrolyte; conductor means for conducting a voltage generated between the first and second electrodes in correspondence with gas properties; and sheath means having a generally tubular wall surrounding the electrodes and electrolyte for supporting the electrodes and electrolyte within the furnace, and wherein said sensor includes:
  a. means for supporting said second electrode on said sheath means;
  b. said second electrode and said electrolyte means having cooperating wall means defining gas passages to allow passage of gas past the points of contact of the second electrode and said electrolyte means and into the interior of the sheath means, and said gas passages affording adequate gas exchange at the contact between the electrolyte and second electrode to minimize chemical reactions and provide representative measurements,
  the improvement wherein said electrolyte means is formed of two parts with said first part being in electrical contact with said first electrode and said second part being sacrificial and separable from said first part and said second part being in electrical contact with said second electrode and said second part being located intermediate said first part and said second electrode at the point of maximum thermal stresses to thermally insulate said first electrolyte part from said second electrode to avoid maximum thermal stress.

14. The improvement of any of claims 1, 7, 12 and 13 wherein said second part is composed of Zirconia doped with $Y_2O_3$ yittria in the range of 3 to 8 mole % $Y_2O_3$.

15. The improvement of any of claims 1, 7, 12 and 13 wherein said second part is composed of Zirconia doped with $Y_2O_3$ yittria in the percent of 3 mole % $Y_2O_3$.

16. In an oxygen sensor for measuring the properties of a gas inside a furnace having a solid electrolyte means with an interior surface and an exterior surface for cooperation with first and second electrodes to generate a representative voltage; a first electrode in contact with the interior surface of the electrolyte; a second electrode having a surface in contact with the exterior surface of the electrolyte; conductor means for conducting a voltage generated between the first and second electrodes in correspondence with gas properties; and sheath means having a generally tubular wall surrounding the electrodes and electrolyte for supporting the electrodes and electrolyte within the furnace, and wherein said sensor includes:

a. means for supporting said second electrode on said sheath means;

b. said second electrode and said electrolyte means having cooperating wall means defining gas passages to allow passage of gas past the points of contact of the second electrode and said electrolyte means and into the interior of the sheath means, and said gas passages affording adequate gas exchange at the contact between the electrolyte and second electrode to minimize chemical reactions and provide representative measurements, the improvement wherein said electrolyte means is provided with a heat resistant fiber jacket.

* * * * *